(12) United States Patent
Amron

(10) Patent No.: US 7,607,851 B2
(45) Date of Patent: Oct. 27, 2009

(54) FOUNTAIN TOOTHBRUSH

(76) Inventor: Scott L. Amron, P.O. Box 544, Plainview, NY (US) 11803

( * ) Notice: Subject to any disclaimer, the term of this patent is extended or adjusted under 35 U.S.C. 154(b) by 0 days.

(21) Appl. No.: 11/821,353

(22) Filed: Jun. 22, 2007

(65) Prior Publication Data

US 2008/0050695 A1    Feb. 28, 2008

Related U.S. Application Data

(63) Continuation-in-part of application No. 11/401,702, filed on Apr. 11, 2006.

(51) Int. Cl.
*A46B 11/00* (2006.01)
(52) U.S. Cl. .................. 401/268; 401/282; 401/289
(58) Field of Classification Search ................ 401/268, 401/270, 282–291
See application file for complete search history.

(56) References Cited

U.S. PATENT DOCUMENTS

| | | | | |
|---|---|---|---|---|
| 1,097,122 | A | * | 5/1914 | Engstrom .................... 401/289 |
| 2,028,519 | A | * | 1/1936 | Peterkin et al. ............... 30/324 |
| 2,548,255 | A | * | 4/1951 | Cressler ........................ 300/21 |
| 3,593,707 | A | * | 7/1971 | Pifer ........................... 601/163 |
| 3,610,234 | A | * | 10/1971 | Oates .......................... 601/155 |
| 3,869,746 | A | * | 3/1975 | Man-king ....................... 15/29 |
| 4,412,823 | A | | 11/1983 | Sakai et al. |
| 4,582,075 | A | * | 4/1986 | O'Neal et al. ............... 132/308 |
| 5,231,978 | A | | 8/1993 | Kao et al. |
| 5,746,595 | A | | 5/1998 | Ford |
| 6,047,429 | A | | 4/2000 | Wu |
| 6,233,773 | B1 | | 5/2001 | Karge et al. |
| 6,357,072 | B1 | | 3/2002 | Zinn |
| 6,689,078 | B1 | | 2/2004 | Rehkemper et al. |

* cited by examiner

*Primary Examiner*—David J Walczak
(74) *Attorney, Agent, or Firm*—Cohen Pontani Lieberman & Pavane LLP

(57) ABSTRACT

A toothbrush body includes a handle connected to a head and bristles projecting from the top of the head. A channel runs longitudinally through the body between a first opening and a second opening such that the first opening is in communication with the second opening through the channel. The channel and the first and second openings are arranged so that a substantially downward running stream of water directed into one of the first opening and the second opening is redirected through the channel and out of the other of the first opening and the second opening to form a fountain. A direction of a flow of the fountain at the other of the first opening and the second opening has an upward component so that a user, i.e., holder of the toothbrush, can easily reach the fountain for oral rinsing.

17 Claims, 8 Drawing Sheets

FOUNTAIN TOOTHBRUSH

CROSS REFERENCE TO RELATED APPLICATIONS

This application is a continuation-in-part of U.S. patent application Ser. No. 11/401,702 which was filed with the U.S. Patent and Trademark Office on Apr. 11, 2006.

BACKGROUND OF THE INVENTION

The present invention relates to a toothbrush having a channel for redirecting at least a portion of a faucet stream.

Brushing teeth is an essential part of any oral hygiene routine. It is recommended that brushing be performed after every meal. However, if a person is not at home, a cup may not be readily available for rinsing after brushing.

Even if a cup is available, cups collect dirt and require frequent cleaning and may not be desirable for use. The use of paper cups solves this problem but is not environmentally friendly as it creates waste. Water directly from a faucet may be used for rinsing. However, it is difficult to get the water from the faucet to a user's mouth without a cup. It is difficult to get enough water using cupped hands. Furthermore, the use of cupped hands may create splashes and spillage. It is also awkward to reach the stream exiting the faucet directly. Accordingly, there is a need for a simple and sanitary means for oral rinsing after brushing.

SUMMARY OF THE INVENTION

An object of the invention is to provide a toothbrush which facilitates oral rinsing without the problems associated with the prior art.

The object is met by a toothbrush having a body having a handle portion connected to a head portion, the body having a top and a bottom, and bristles projecting from the top of said head portion. The body defines a channel having a first end and a second end such that said first end is in communication with said second end through said channel.

The channel and the first and second ends are arranged so that a substantially downward running stream of water directed into one of the first end and the second end is redirected through the channel and out of the other of the first end and the second end to form a fountain. A direction of a flow of the fountain at the other of the first end and the second end has an upward component so that a user, i.e., holder of the toothbrush, can easily reach the fountain for oral rinsing.

According to one embodiment, the direction of the flow of the fountain at the other of the first end and the second end is approximately perpendicular to a longitudinal axis of the handle at the other of the first end and the second end. Alternatively, the direction of flow of the fountain at the other of the first end and the second end may have a component directed toward the second end of the handle distal from the head.

In one embodiment, both the first and second ends are arranged on one side, i.e., on the top or on the bottom of the handle. The channel may be arranged in the handle or in the head of the body. Instead of being arranged at the top or bottom of the body, at least one of the channel ends may be arranged at an end of the body.

In one embodiment, the channel is a closed channel which extends through the body between two holes or openings in the body. In this embodiment, the ends of the channels are defined by the holes or openings in the body. This channel may run the entire length of the body, or a portion of the length of the body. The channel may alternatively be an open channel running along a length of the toothbrush body.

The channel may be incorporated in an electric toothbrush. The toothbrush may further comprise a pump arranged in the handle for pumping fluid in the channel toward the second opening. An electric motor is connected to the pump for driving the pump. The electric motor may further be connected to movable bristles for driving movement of the bristles.

The second opening may be smaller than the first opening to facilitate collection of water at the first opening and to provide sufficient velocity of the fluid flowing out of the second opening. A ratio of an area of the first opening to an area of the second opening is in the range of 1 to 16.

In a further embodiment, a cavity is defined in the toothbrush having an opening arranged at the head or the handle portion. The cavity allows a user to collect water from a faucet and bring the water to the user's mouth for rinsing.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views.

DETAILED DESCRIPTION OF THE PRESENTLY PREFERRED EMBODIMENTS

Figure 1:
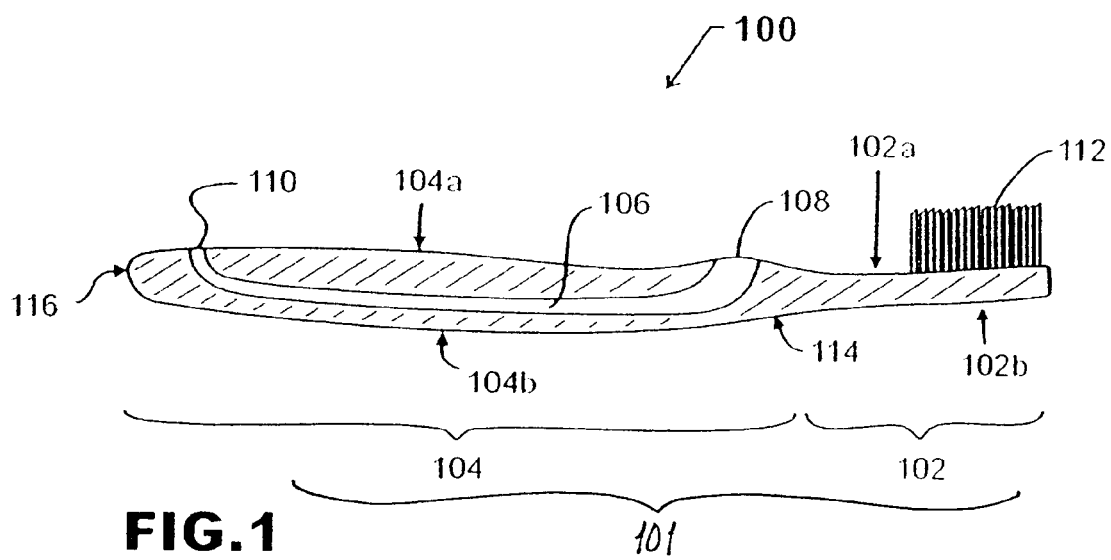
FIG. 1 is a longitudinal sectional view of a toothbrush according to an embodiment of the present invention.
Figure 2:
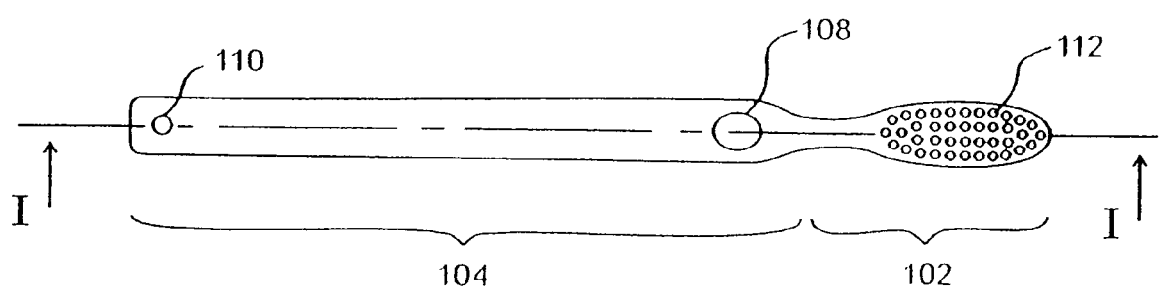
FIG. 2 is a plan view of the toothbrush of FIG. 1.

FIGS. 1 and 2 show a toothbrush 100 according to an embodiment of the present invention. The toothbrush has a body 101 including a handle 104 and a head 102. The handle 104 includes a top 104a and a bottom 104b. Likewise, the head 102 includes a top 102a and a bottom 102b. Bristles 112 are arranged on the top 102a of the head 102.

The handle 104 has a first end 114 proximate the head 102 and a second end 116 arranged distally from the head 102. A channel 106 extends longitudinally through the handle 104 between a first opening 108 and a second opening 110. Both the first and second openings are arranged on the top side 104a of the handle 104.

Figure 3:
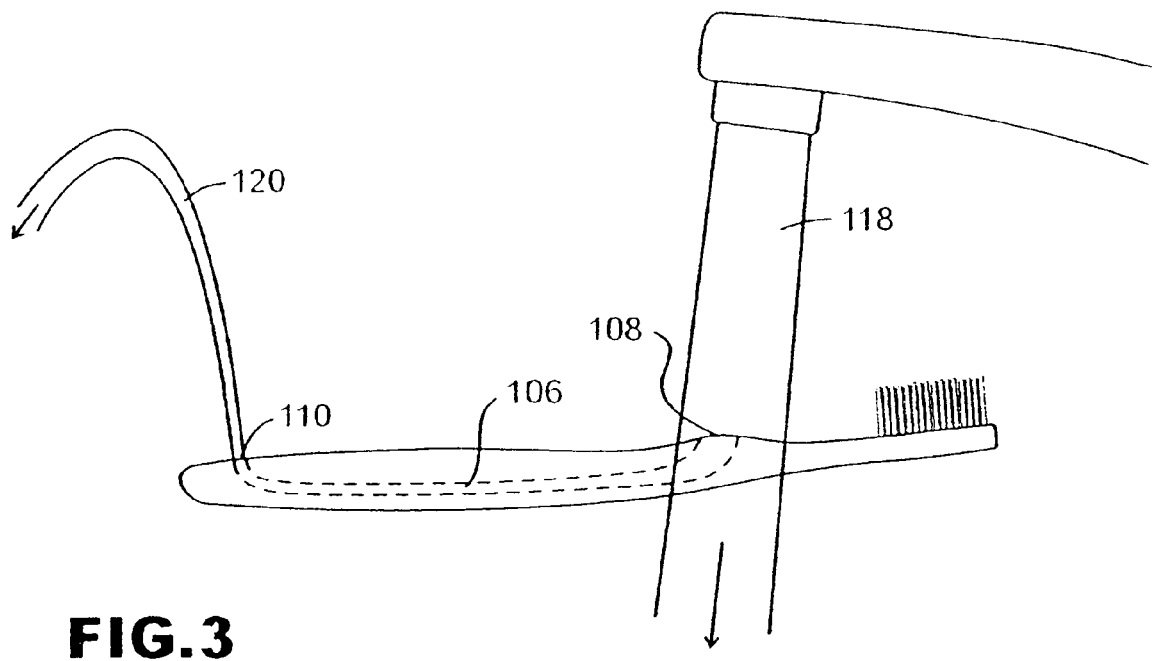
FIG. 3 is a side view of the toothbrush of FIGS. 1 and 2 held under a faucet.

As shown in FIG. 3 the first opening 108 is placed facing upstream in a water stream 118 flowing from a faucet. At least a portion of the water stream 118 enters the channel 106 through opening 108 and is redirected through the channel 106 to form a fountain 120 flowing out of the opening 110 in the top 104a of the handle 104. As shown in FIG. 3, the fountain 120 is directed upwards and toward the second end 116 of the handle 104. The channel 106 and second opening 110 may alternatively be arranged so that the fountain flows out of the second opening in a direction that is approximately perpendicular to the top 104a of the handle 104. The toothbrush may alternatively or additionally be designed so that the water stream 118 directed into the second opening creates a fountain directed upward from the first opening.

The handle 104 of the toothbrush 100 in FIGS. 1 and 2 is preferably translucent, at least in the area of the channel 106, so that a user can detect the presence of any dirt, mold, or other obstruction in channel 106, and thus relieves any sanitary concerns that an otherwise reluctant user might have. Furthermore, the handle 104 may be made of a material that does not promote the growth of molds such as, for example, nylon. Mold requires some food to grow. Therefore, at least the portion of the toothbrush defining the channel is preferably made of nylon or another material having a slick or non-sticking surface which allows food to easily wash off and thereby prevents mold growth. This is the preferred material for all embodiments of the channel described herein. Moreover, the arrangement of the channel along the longitudinal extent of the toothbrush allows any water in the channel to drip out when the toothbrush rests upright in a holder.

The size of the first and second openings 108, 110 and the cross-section of the channel 106 must be small enough so that the overall size of the handle is small enough to fit in a toothbrush holder, and must be large enough to supply a sufficient amount of water for oral rinsing. Furthermore, the first opening 108 may be larger than the second opening 110 to facilitate collection of water from the faucet stream 118 and increase the velocity of the water exiting the second opening 110. The ratio of the diameters of the first opening to that of the second opening is in the range of 1 to 4. Accordingly, the area of the first opening 108 may be up to 16 times as large as that of the second opening 110. In a specific embodiment, the openings 108, 110 are circular, the diameter of the second opening 110 is approximately 3.35 mm, and the diameter of the first opening is approximately 10.0 mm. Since the diameter of the first opening is approximately three times the diameter of the second opening, the area of the first opening is approximately nine times the area of the first opening. Although the openings 108 and 110 are depicted as being circular, the openings may also be oblong or oval to better fit within the width of the handle 104.

Figure 4:
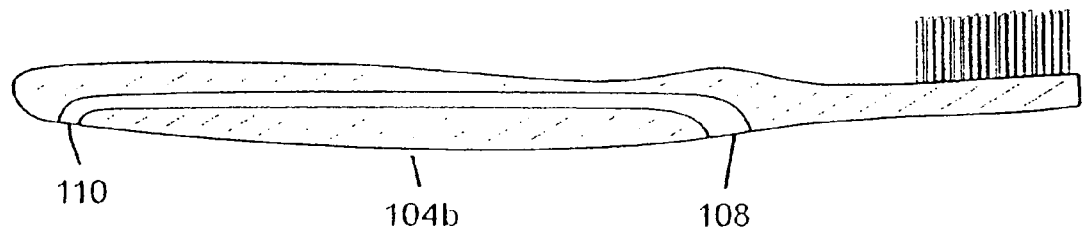
FIG. 4 is a longitudinal sectional view of a toothbrush according to another embodiment of the present invention.
Figure 5:
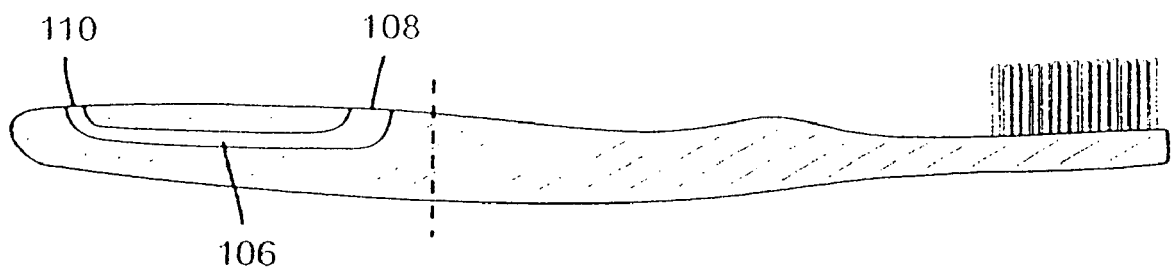
FIG. 5 is a sectional view of a toothbrush according to yet another embodiment of the present invention.

During brushing, it is possible that toothpaste and/or toothpaste suds may enter the channel 106 through the openings 108, 110. However the toothpaste and toothpaste suds are prevented from accumulating in the channel 106 because the user rinses the channel 106 each time the user orally rinses. Nonetheless, it may be desirable to prevent the entrance of toothpaste and/or toothpaste suds into the channel so that the fountain 120 includes only clean water. FIG. 4 shows a further embodiment in which the openings 108 and 110 are arranged at a bottom 104b of the handle 104 to prevent toothpaste and/or toothpaste suds from entering the channel during brushing. Another way to prevent toothpaste suds from entering the channel is to relocate the first opening closer to the distal end 116 (e.g., a position approximately in the middle of the longitudinal length of the handle 104). According to a further embodiment, the distance between the bristles 112 and the first opening is at least 5 cm. In a preferred embodiment, the distance of the first opening 108 from the bristles 112 is at least ⅓ of the distance from the bristles 112 to the second end 116 of the handle 104. In yet another embodiment, both the first and second openings 108, 110 are arranged on the half of the handle that is distal from the head as shown in FIG. 5.

Figure 6A:
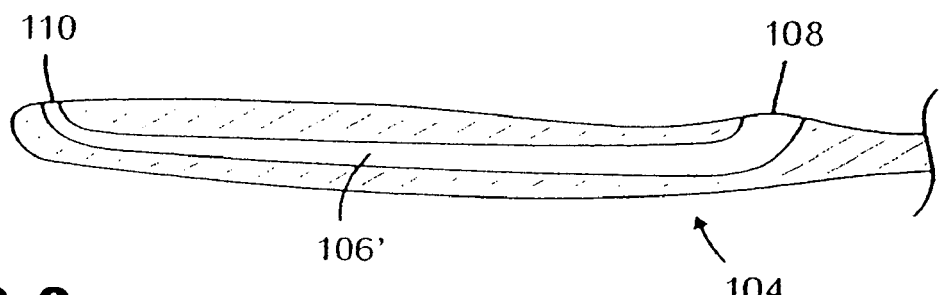
FIGS. 6a and 6b are sectional views of handles showing features of the channel according to two embodiments of the present invention.
Figure 6B:
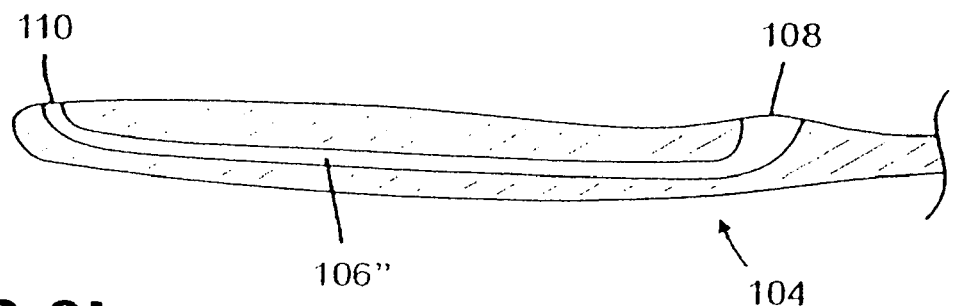

The channel 106 may be gradually tapered along its length from the diameter of the first opening 108 to the diameter of the second opening 110 as shown in FIG. 6a. Alternatively, the end of channel 106 may taper to the diameter of the second opening so that the entire length of the longitudinal extension of the channel 106 through the handle 104 has constant cross-section as shown in FIG. 6b. Although the openings are assumed to be circular in this embodiment, the openings 108, 110 and the cross section of the channel 106 may comprise any shape.

Figure 7:
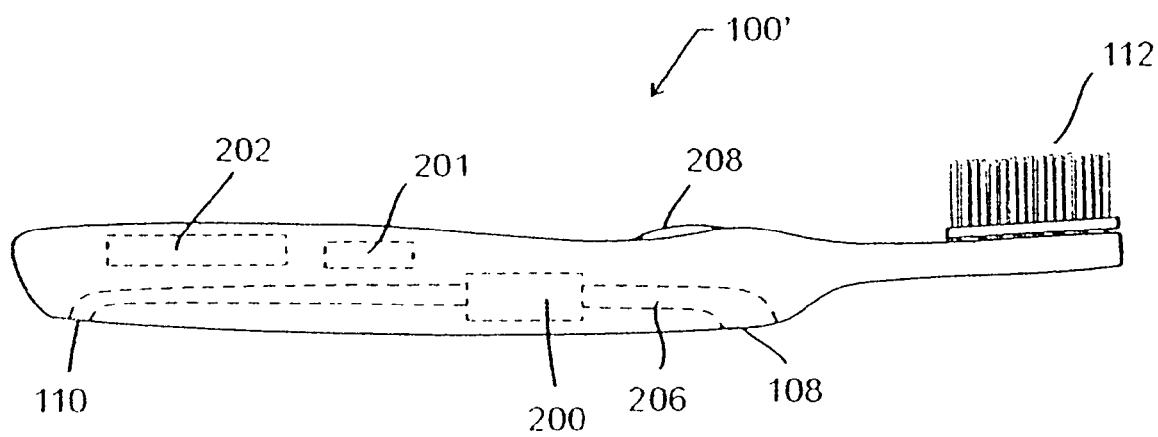
FIG. 7 is a sectional view of yet another embodiment of the toothbrush according to the present invention.
Figure 8:
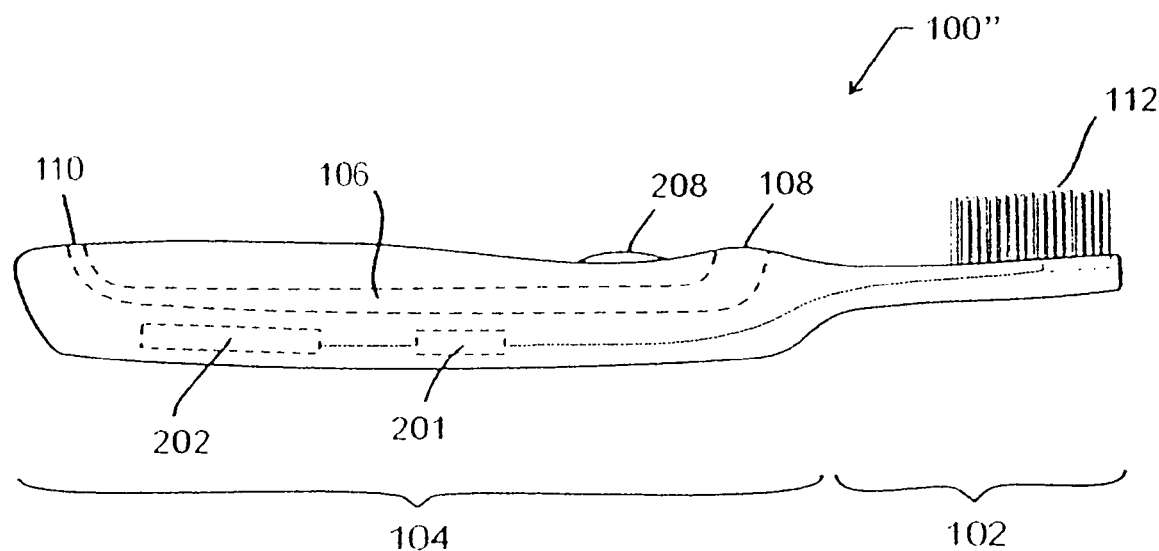
FIG. 8 is a sectional view of yet another embodiment of the toothbrush according to the present invention.

FIG. 7 discloses a further embodiment in which a channel 206 is connected between openings on a bottom side 104b of a handle 104. Furthermore, a pump 200 is added to the channel 106. The pump may for example include a pump as disclosed in U.S. Pat. No. 6,047,429, the entire contents of which are incorporated herein by reference. The pump may alternatively comprise any known or hereafter developed pump. This embodiment is useful when the stream 118 flowing from the faucet or other source has low pressure. A battery power supply 202 may be incorporated into the toothbrush. Alternatively, the toothbrush 100' may have a connection for an external power source (not shown). An electric motor 201 drives the pump 200. The electric motor may optionally also drive movement of the bristles 112. A switch 208 is operatively connected to the motor 201 so that a user can selectively turn the pump 200 on and off. The channel 106 may also be incorporated into an electric toothbrush without the pump. FIG. 8 shows another embodiment in which the channel 106 and openings 108, 110 as shown in FIG. 1 are incorporated in an electric toothbrush 100". In this embodiment, the battery 202 and motor 201 are used for moving the bristles 112 and are not connected to a pump for moving the flow of the water through the channel 106. Although the openings 108 and 110 are shown on the top side, the openings may alternatively be arranged on the bottom side as in the embodiment of FIG. 7.

Figure 9:
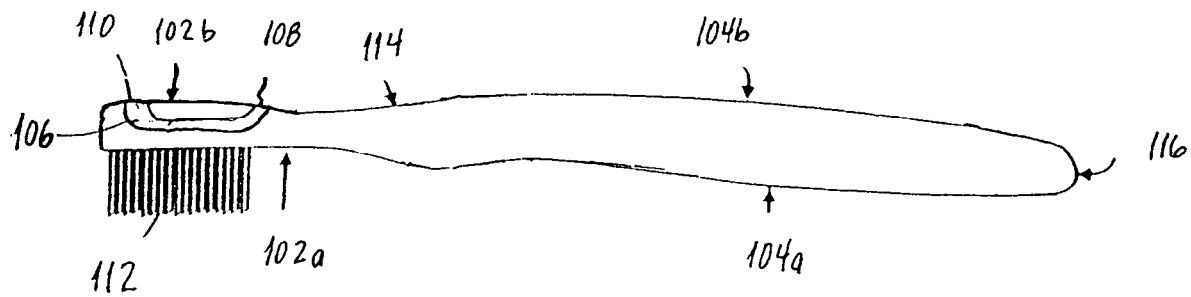
FIG. 9 is a longitudinal sectional view of a further embodiment of the toothbrush according to the present invention.

Although the channel 106 is arranged in the handle 104 of the toothbrush in the previous embodiments, the channel 106 may alternatively be arranged at the head 102 as shown in FIG. 9. This embodiment allows a user to merely flip the toothbrush 100 upside-down to use the channel 106 when the user is holding the toothbrush for brushing teeth. The first and second opening 108, 110 may be configured as in the previously described embodiments. For example, the flow out of the exit hole may be directed toward the head end 115, perpendicularly to the bottom 102b, or toward the handle 104. The first or second opening 108, 110 may be the input for receiving the water stream. The opening designed as the input may be larger than the exit opening to facilitate collection of water from the faucet stream. Furthermore, the shape of the openings 108, 110 and cross-section of the channel 106 may comprise any shape aesthetically and/or operationally suitable for the purposes described above. For example, the openings 108 and 110 may be polygon-shaped such as, for example, star-shaped for a children's toothbrush. Furthermore, each of the embodiments described above includes one channel having one hole at each end of the channel. Alternatively, the toothbrush may have a plurality of channels running side-by-side through the toothbrush. As another alternative, the toothbrush may define plural holes at each end of the channel.

Instead of being arranged exclusively in the head 102 or in the handle 104, the channel 106 may extend from the head 102 to the handle 104. Furthermore, the channel 106 is depicted, for example, in FIGS. 1 and 9 as being substantially straight between the two ends 108, 110. However, the channel path may alternatively be formed as a curved section or an arc between the two ends. As a further alternative, the channel 106 may include any combination of straight and curved sections.

Figure 10:
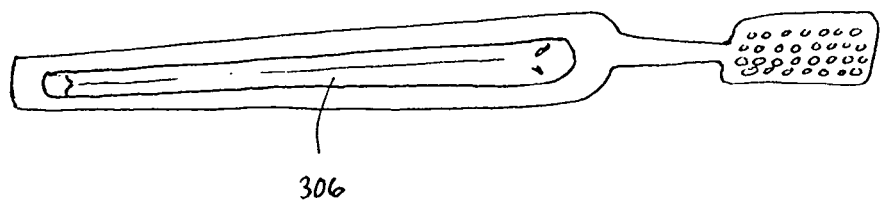
FIG. 10 is a plan view of a toothbrush according to another embodiment.
Figure 11:
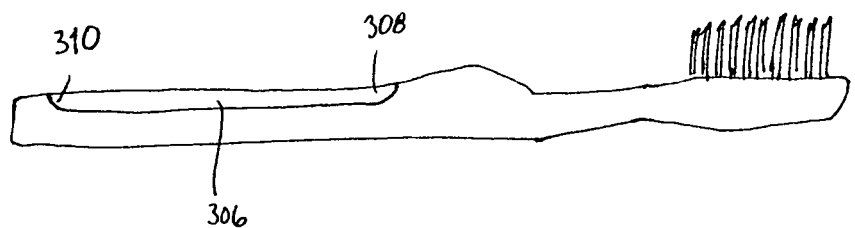
FIG. 11 is a sectional view of the toothbrush of FIG. 10.

According to yet another embodiment depicted in FIGS. 10-11, a channel 306 is arranged as a groove in a surface of the toothbrush. This allows the channel to be easily cleaned by a user. In this embodiment, a first end 308 of the groove 306 is placed in a water stream under a faucet such that the groove directs a portion of the water stream to the second end 310 of the groove. The second end 310 of the groove is shaped so that a stream of water flowing down the groove toward the second end 310 forms a fountain as the stream exits the second end 310. The first end 308 may alternatively or additionally be similarly shaped to form a fountain when the fluid flows toward the first end 308. The groove 306 may have a constant cross section or a variable cross section that decreases or increases from the first end 308 to the second end 310. Furthermore, the cross-sectional shape of the groove may be semicircular, or any other shape. Although the groove 306 is shown on the top of the handle, the groove 306 may be arranged at any location on the toothbrush. Furthermore, the groove does not necessarily extend over the entire length of the handle.

Figure 11A:
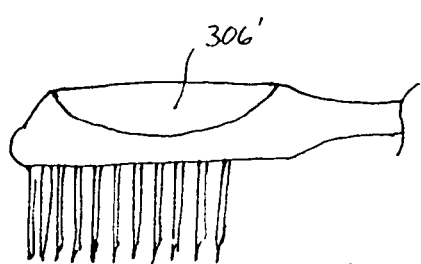
FIG. 11a is a sectional view of another embodiment of a toothbrush according to the present invention.
Figure 11B:
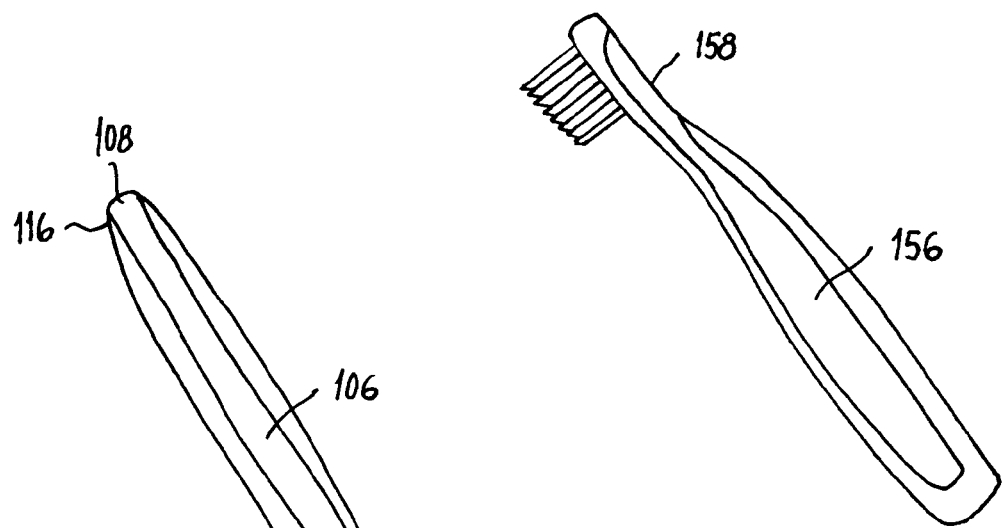
FIG. 11b is a sectional view of another embodiment of a toothbrush according to the present invention.

FIG. 11a shows an embodiment with a groove 306' arranged on a head of a toothbrush. In this embodiment, the groove 306' is shaped in the form of a scoop, cavity, or a bowl. Instead of being used as a fountain, such a groove may alternatively be used as a trough which is filled from a faucet and brought to a user's mouth. As a further alternative, FIG. 11b discloses an interior space or cavity 156 defined within the toothbrush for collecting water through opening 158. In this embodiment, more water can be collected than the open trough. Although FIG. 11b depicts the opening 158 as being arranged at the bottom side of the head end, the opening 158 can be arranged at any location such as, for example, the distal end of the handle.

Figure 12:
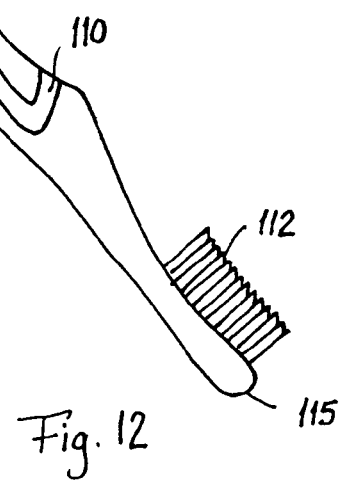
FIG. 12 is a sectional view of a further embodiment of a toothbrush according to the present invention.
Figure 13:
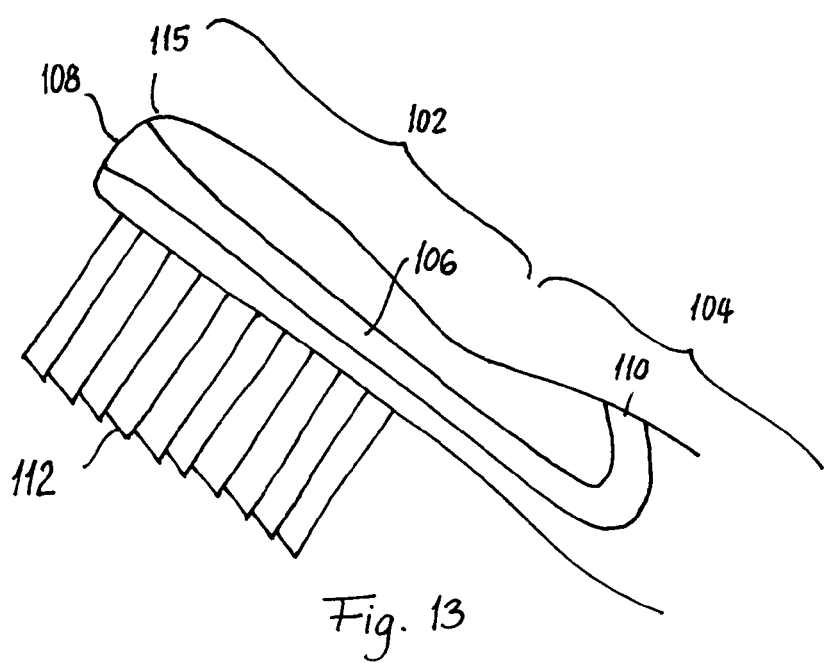
FIG. 13 is a sectional view of yet another embodiment of a toothbrush according to the present invention.

In yet a further embodiment shown in FIG. 12, one of the ends 108 of the channel 106 is arranged at the handle end surface 116 of the handle 104 that is distal from the head 102. In this embodiment, the path of the channel 106 through the toothbrush body 101 is J-shaped so that when the end 116 is held in a water stream with the end 108 facing upstream, a fountain is produced at the other end 110, or vice versa. This J-shaped embodiment of the channel 106 may alternatively be implemented with the end 108 facing the head end surface 115 as shown in FIG. 13. Furthermore, the embodiment of FIG. 13 shows that the channel 106 extends from the head 102 into the handle 104. Although the embodiments of the channel 106 shown in FIGS. 1-12 are arranged in either the head 102 or the handle 104, any of these embodiments of the channel 106 may alternatively be arranged so that the channel extends at least partially in each of the head 102 and the handle 104.

Figure 14:
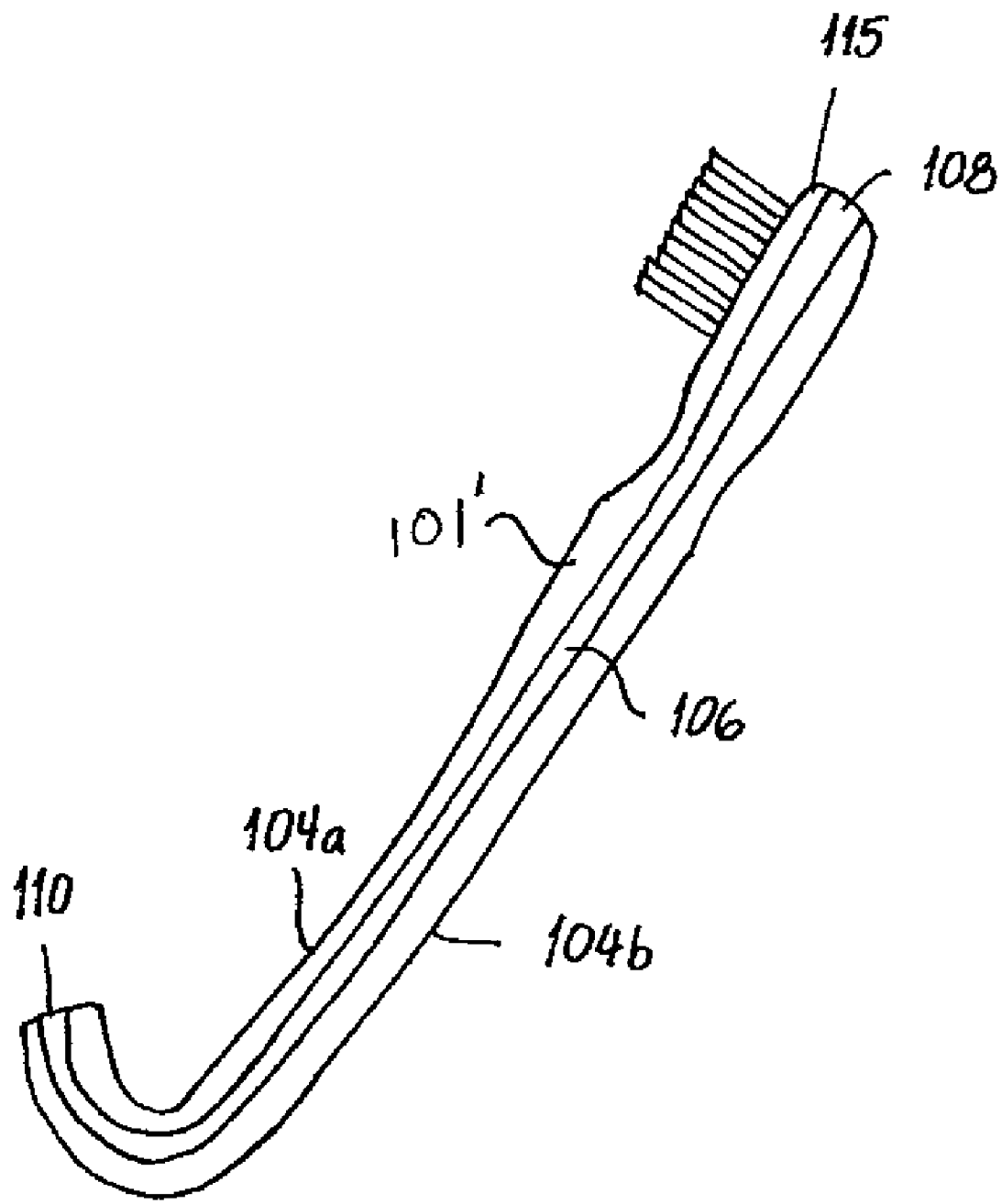
FIG. 14 is a section view of still another embodiment of a toothbrush according to the present invention.

In yet a further alternative embodiment, the channel 106 may extend between the two ends of the toothbrush body 101', as shown in FIG. 14. In this embodiment, the body 101' itself is J-shaped. Although the opening 110 is arranged on a top 104a of the handle 104 in FIG. 14, the opening 110 may alternatively face the bottom 104b of the handle 104. The opening 108 may alternatively be arranged on the body, as shown, for example, in FIG. 1.

Figure 15:
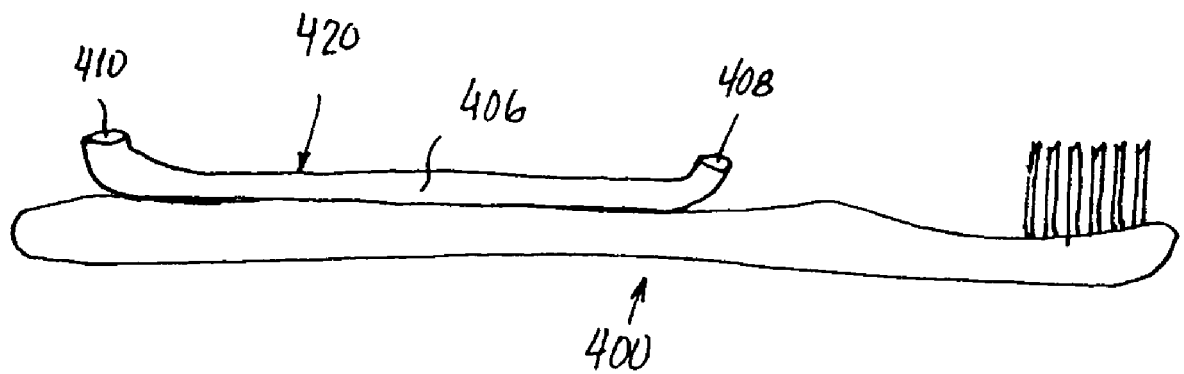
FIG. 15 is a side view of another embodiment of a toothbrush according to the present invention.
Figure 16:
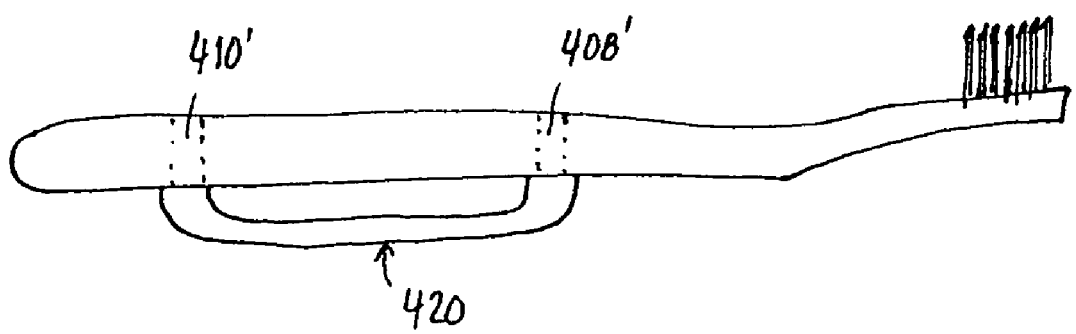
FIG. 16 is a side view of yet another embodiment of the present invention.

FIGS. 15 and 16 show embodiment in which a conduit forming a channel is arranged on a conventional toothbrush. In FIG. 15, a conduit 420 is arranged on a handle of a toothbrush 400. The conduit 420 defines a channel 406 therethrough between ends 408, 410. In this embodiment, a section of the conduit 420 between the ends 408, 410 is connected to the toothbrush using adhesive or any other known or hereafter developed attachment means. Although the conduit is depicted as being arranged on the handle portion of the toothbrush, the conduit 420 may also be arranged on the bottom side of the head of the toothbrush. FIG. 16 shows another embodiment in which the ends of the conduit 420 are connected to the tooth brush at holes 408' and 410' which extend through the toothbrush.

In each of the above embodiments, the channels are depicted as opening or being open on the top or bottom of the toothbrush. However, the channel could alternatively be arranged to open or be open along either side of the toothbrush.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A toothbrush, comprising a body having a handle portion connected to a head portion, the body having a top and a bottom, and bristles projecting from the top of said head portion, said body having a channel therethrough with a first end and a second end such that said first end is in communication with said second end through said channel, wherein said channel and said first and second ends are arranged so that at least a portion of a substantially downward running stream of water directed into one of said first end and said second end is redirected though said channel and out of the other of said first end and said second end to form an upwardly directed fountain, thereby availing to a user of the toothbrush a supply of water for rinsing, wherein the first end and the second end are at least one of arranged on a same side of the body opening in the substantially same direction and connected to one another by the channel having an acute angle.

2. The toothbrush of claim 1, wherein at least one of said first and second ends are arranged on said head portion.

3. The toothbrush of claim 1, wherein both of said first and second ends are arranged on said head portion.

4. The toothbrush of claim 1, wherein said channel comprises an enclosed channel extending through said body, said first and second ends comprising first and second openings.

5. The toothbrush of claim 4, wherein said one of said first opening and said second opening is smaller than the other of said first opening and said second opening.

6. The toothbrush of claim 5, wherein a ratio of an area of said one of said first opening and said second opening to the other of said first opening and said second opening is in the range of 1 to 16 mm.

7. The toothbrush of claim 5, wherein an area of said one of said first opening and said second opening is approximately three times greater than an area of the other of said first opening and said second opening.

8. The toothbrush of claim 4, wherein at least one of the first and second openings is arranged on said head portion.

9. The toothbrush of claim 4, wherein the first and second openings are arranged on said head portion.

10. The toothbrush of claim 4, wherein said channel is defined by a conduit connected to said toothbrush.

11. The toothbrush of claim 1, wherein said toothbrush further comprises an electric motor having connections for receiving an electric power supply, and movable bristles actuatable by said electric motor.

12. The toothbrush of claim 11, further comprising a pump arranged to pump fluid in said channel, said electric motor being drivably connected to said pump.

13. The toothbrush of claim 1, wherein said head portion has a head end surface facing away from said handle portion and said handle portion has a handle end surface facing away from said head portion, wherein said one of said first end and said second end is arranged on said head end surface or said handle end surface.

14. The toothbrush of claim 13, wherein the channel runs along a J-shaped course through said body.

15. The toothbrush of claim 13, wherein the first and second ends of said channel are arranged at the handle end surface and the head end surface, respectively.

16. A toothbrush, comprising a body having a handle portion connected to a head portion, the body having a top and a bottom, and bristles projecting from the top of said head portion, said body defining a cavity through the body having a first opening and a second opening, whereby downward flowing water entering the cavity through one of the first and second openings from a faucet is transportable by the user to the user's mouth for rinsing, the flowing water exits the other of the first and second openings in an upward flow, wherein one of the cavity and the body is J-shaped between the first and second openings.

17. The toothbrush of claim 16, wherein one of said first and second openings said opening is defined in said head portion of said toothbrush and said cavity extends at least partially into said handle portion.

* * * * *